United States Patent
Hameed et al.

(10) Patent No.: US 8,172,787 B2
(45) Date of Patent: May 8, 2012

(54) METHOD AND APPARATUS TO DETECT BIOCONTAMINATION IN AN INSUFFLATOR FOR USE IN ENDOSCOPY

(75) Inventors: Salmaan Hameed, San Jose, CA (US); Amit A. Mahadik, San Jose, CA (US); Abhishek Gattani, San Jose, CA (US); Natraj Iyer, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 169 days.

(21) Appl. No.: 11/279,723

(22) Filed: Apr. 13, 2006

(65) Prior Publication Data
US 2007/0244424 A1 Oct. 18, 2007

(51) Int. Cl.
A61M 37/00 (2006.01)
A61M 31/00 (2006.01)
A61M 25/00 (2006.01)

(52) U.S. Cl. ............ 604/26; 604/506; 604/264
(58) Field of Classification Search ......... 604/23–26, 604/65–67, 506, 264
See application file for complete search history.

(56) References Cited

U.S. PATENT DOCUMENTS

| | | | | | |
|---|---|---|---|---|---|
| 5,246,419 | A | * | 9/1993 | Absten | 604/26 |
| 5,328,847 | A | * | 7/1994 | Case et al. | 205/778 |
| 5,360,396 | A | * | 11/1994 | Chan | 604/26 |
| 6,068,609 | A | * | 5/2000 | Ott et al. | 604/26 |
| 6,632,194 | B1 | * | 10/2003 | Mehner et al. | 604/26 |
| 6,751,491 | B2 | * | 6/2004 | Lew et al. | 600/345 |
| 7,393,345 | B2 | * | 7/2008 | Yang | 604/199 |
| 2002/0026111 | A1 | * | 2/2002 | Ackerman | 600/347 |
| 2003/0187471 | A1 | * | 10/2003 | Cooper | 606/185 |
| 2004/0039779 | A1 | | 2/2004 | Armstrong et al. | |
| 2004/0254524 | A1 | * | 12/2004 | Spearman et al. | 604/26 |
| 2005/0137529 | A1 | * | 6/2005 | Mantell | 604/129 |
| 2007/0249990 | A1 | * | 10/2007 | Cosmescu | 604/27 |
| 2008/0288578 | A1 | | 11/2008 | Silfverberg | |

OTHER PUBLICATIONS

Jacob, Rebecca. Kumaresh, V. Medical Grade Compressed Air. 2001. Practical Procedures. 13:2. p. 1.*
Hubar, Sean. Pelon, William. Gardiner, Diana. Evaluation of Compressed Air Used in the Dental Operatory. 2002. Journal of the American Dental Association. 33:7. 837-841.*
"Honey . . . I've shrunk the lab!," Explosion, Aug. 2005, pp. 1-4, Issue 10, Interactive Design by Apical, downloaded from http://www.a-star.edu.sg/explosion/iss10/honey.htm.
"Researchers target silicon chips for biomolecular devices," Physorg.com, Nov. 1, 2005, pp. 1-4, downloaded from http://www.physorg.com/news7768.html.
"Labs-on-a-chip to Detect Milk Contamination," ScienceDaily, May 14, 2004, pp. 1-2, ScienceDaily LLC, downloaded from http://www.sciencedaily.com/releases/2004/05/040517072519.htm.

(Continued)

Primary Examiner — Kevin C Sirmons
Assistant Examiner — William Carpenter
(74) Attorney, Agent, or Firm — Blakely, Sokoloff, Taylor & Zafman LLP.

(57) ABSTRACT

An apparatus to provide a regulated pressurized gas for introduction into the body of a patient during a medical procedure comprises an internal flow path through which to convey the pressurized gas, a regulator in the flow path to regulate the pressurized gas, and a biosensor to detect a body substance entering or in proximity to the flow path.

1 Claim, 2 Drawing Sheets

OTHER PUBLICATIONS

Elizabeth A. Thomson, "Microchip stores, releases chemicals for many uses," Massachusetts Institute of Technology News Office, Feb. 3, 1999, pp. 1-3, downloaded from http://web.mit.edu/newsoffice/1999/chip-0203.html.

Blaine Friedlander, "Cornell-developed biosensors detect *E. coli* in food," Cornell Chronicle, Apr. 16, 1998, pp. 1-2, downloaded from http://www.news.cornell.edu/Chronicle/98/4.16.98/biosensors.html.

Kent R. Foster, Contamination of Laparoscopic Insufflators with Patient Fluids, Health Canada, No. 106, Minister of Supply and Services, Feb. 13, 1995, 2 pages.

* cited by examiner

METHOD AND APPARATUS TO DETECT BIOCONTAMINATION IN AN INSUFFLATOR FOR USE IN ENDOSCOPY

FIELD OF THE INVENTION

At least one embodiment of the present invention pertains to equipment used for endoscopic medical procedures, and more particularly, to an advanced insulator for endoscopy.

BACKGROUND

Endoscopy in the medical fields allows internal structures of a patient's body to be viewed without the use of traditional, fully-invasive surgery. Endoscopy is widely used to perform many types minimally-invasive medical procedures, such as arthroscopy, laparoscopy, gastroscopy, colonoscopy, etc. A basic tool of endoscopy is the endoscope ("scope"), which contains a set of optics through which internal features of a patient's body can be viewed (typically, with the aid of a special-purpose video camera attached to the endoscope and an appropriate video monitor), when the endoscope is partially inserted into the patient's body.

A supporting device commonly used in certain forms of endoscopy is an insulator. An insufflator is an electromechanical device which pumps sterile gas, typically carbon dioxide, into the body of the patient in the region where the scope is inserted. The purpose is to create more space within the body cavity for the surgeon to see anatomical features and manipulate his instruments. An insulator is commonly used in laparoscopy, for example.

The primary component(s) in a insufflator is/are one or more pressure regulators (connected in series if there is more than one) to regulate the pressure level of the gas.

During endoscopic surgery, the pressure within the body occasionally and momentarily may be greater than at the output of the insulator at a particular instant in time. When this happens, gas and/or or biocontamination (e.g., body fluid) can travel back through the external gas conduit toward the insulator ("backflow"). If biocontamination reaches the insufflator, contamination of the insulator can occur, which necessitates a delay in the procedure, possibly putting the patient at greater risk and, at the very least, complicating cleaning and sterilization of the equipment. With conventional insufflators, there is no easy way to determine whether backflow contains biocontamination or merely sterile gas, other than by visual inspection. Visual inspection, however, can be difficult and inaccurate. Some systems use a humidity detector to detect indirectly the possible presence of backflow; however, that is not a very accurate detection method, at least because it cannot directly detect the presence of biocontamination. Among other reasons, a humidity detector cannot reliably detect the presence of biological particulate matter independently of body fluid. There may be other reasons why it may be undesirable to base the detection of biocontamination or backflow on humidity.

In addition, biocontamination can be present in the gas supply that is input to the insulator. Known conventional insufflators, however, have no way of detecting this mode of biocontamination.

SUMMARY OF THE INVENTION

The present invention includes an apparatus to provide a regulated pressurized gas for introduction into the body of a patient during a medical procedure. The apparatus comprises an internal flow path through which to convey the pressurized gas, a regulator in the flow path to regulate the pressurized gas, and a biosensor to detect biocontamination in proximity to the flow path.

Other aspects of the invention will be apparent from the accompanying figures and from the detailed description which follows.

BRIEF DESCRIPTION OF THE DRAWINGS

One or more embodiments of the present invention are illustrated by way of example and not limitation in the figures of the accompanying drawings, in which like references indicate similar elements and in which.

DETAILED DESCRIPTION

An improved insulator for endoscopy is described. References in this specification to "an embodiment", "one embodiment", or the like, mean that the particular feature, structure or characteristic being described is included in at least one embodiment of the present invention. Occurrences of such phrases in this specification do not necessarily all refer to the same embodiment.

Figure 1:
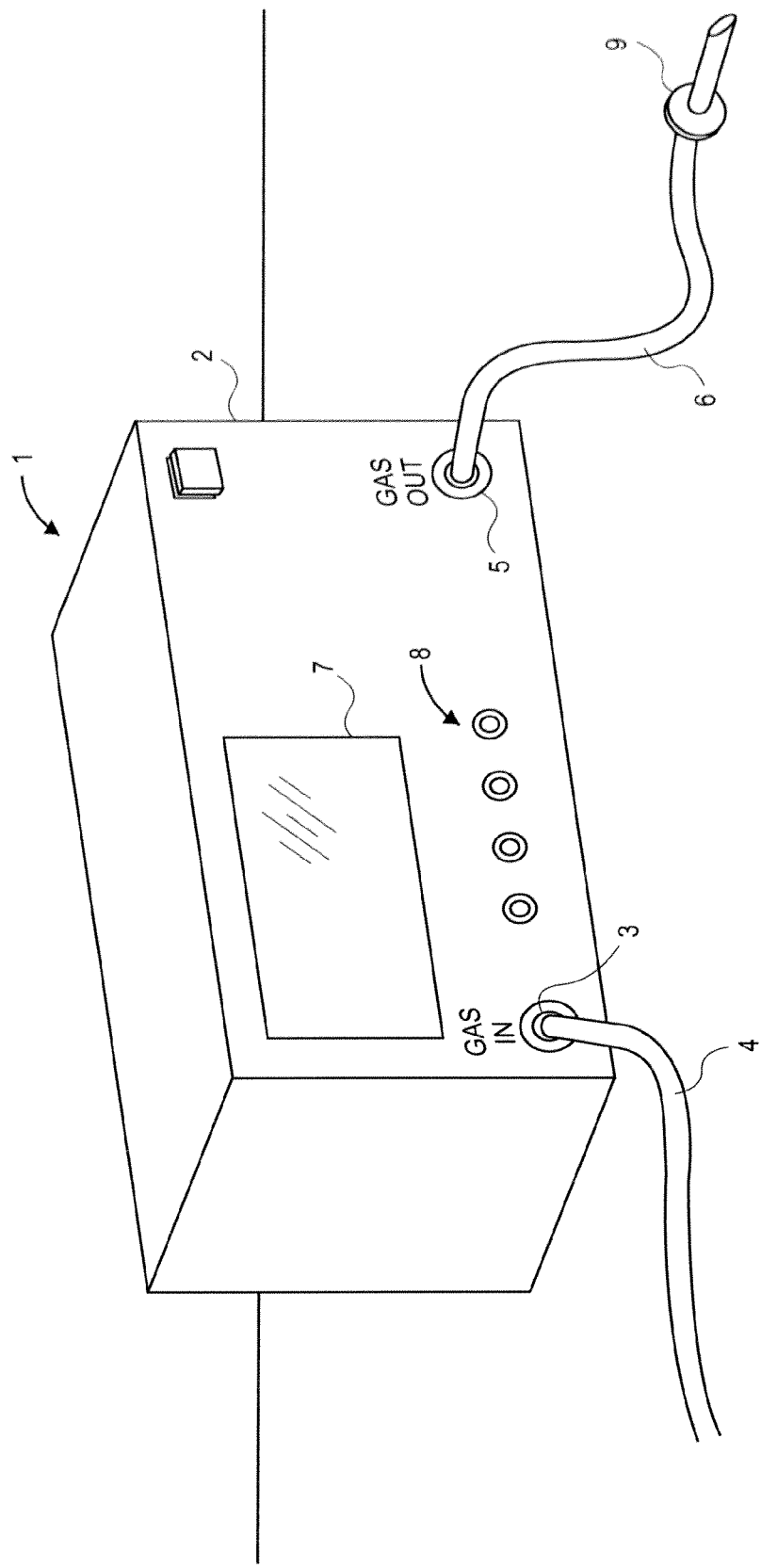
FIG. 1 illustrates an example of some of the external features of an insulator, according to certain embodiments of the invention.

Refer now to FIG. 1, which shows an example of some of the external features of an insulator, according to certain embodiments of the invention. The insufflator 1 has a housing 2, within which are contained one or more pressure regulators and flow rate regulators and other components (not shown in FIG. 1). The housing 1 has a gas input interface 3 at which a flexible gas conduit 4 is connected to receive the gas from an external gas canister (not shown) and a gas output port 5 at which another flexible gas conduit 6 can be connected to provide gas to the patient. Conduit 6 terminates in a trocar 9 or other similar device, which can be considered part of the conduit 6. Visible on the exterior of the insufflator 1 is the display area 7 of a display unit, which may be, for example, a touchscreen liquid crystal display (LCD) device. Most if not all of the features and functions of the insufflator 1 can be controlled through a graphical user interface (GUI) presented on the display unit. Nonetheless, various other manual controls and/or indicators 8 may also be provided on the exterior of the insufflator 1, as a secondary way of controlling certain features and functions or as a way to control other features and functions.

Figure 2:
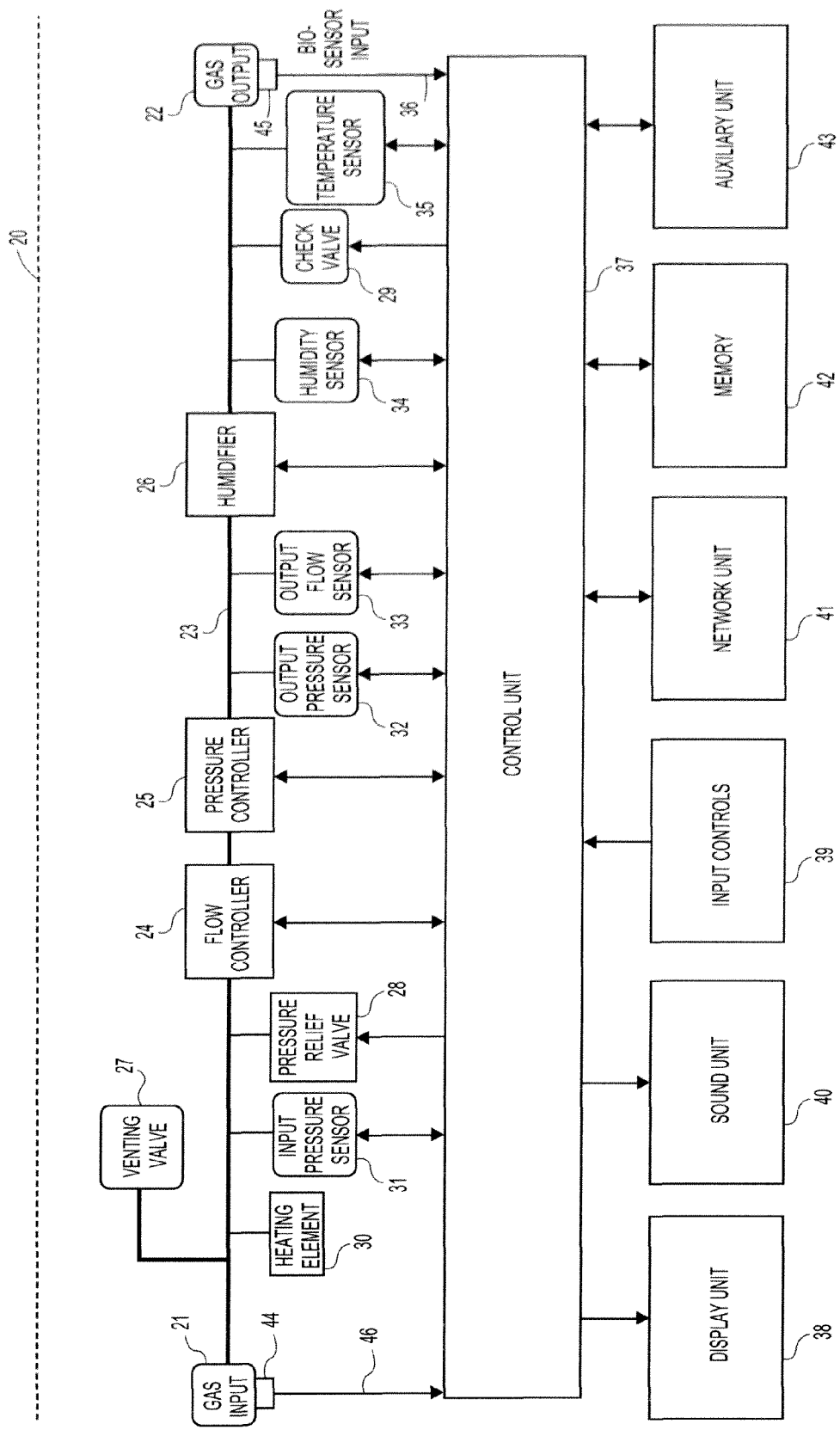
FIG. 2 is a block diagram showing internal components of an insufflator according to certain embodiments of the invention.

FIG. 2 is a block diagram showing internal components of an insufflator according to certain embodiments of the invention, which can be an insufflator such as shown in FIG. 1. The insufflator 20 in FIG. 2 includes a gas input port 21, a gas output port 22, and a gas flow path 23 coupled between the gas input port 21 and the gas output port 22. In operation, the gas canister that provides the gas supply (not shown) is connected to the gas input port 21, either directly or indirectly through a gas conduit (e.g., a hose). The insulator 20 further includes a flow controller 24, pressure controller 25 and a humidifier 26, coupled in series with each other in the gas flow path 23. The pressure controller 25 is coupled to the output of the flow controller 24. The humidifier 26 is coupled to the output of the pressure controller 25.

Also connected to the gas flow path 23 between the gas input port 21 and the flow controller 24 are a venting valve 27, a pressure relief valve 28, and a check valve 29; a heating element 30 to maintain the gas at a predetermined temperature, and an input pressure sensor 31. Further connected to the gas flow path 23 between the gas output of the pressure controller 25 and the input of the humidifier 26 are an output pressure sensor 32 and an output flow sensor 33. In addition, coupled to the gas flow path 23 between the gas output of the humidifier 26 and the gas output port 22 are a humidity sensor 34 and a temperature sensor 35.

It is desirable to be able to accurately and promptly detect the presence of biocontamination (e.g., from the patient's body and/or the gas supply) before it can enter the insufflator 20. Therefore, a first biosensor 44 is provided in the insulator 20 to detect biocontamination in the gas supply that is input to the insufflator 20, while a second biosensor 45 is also provided in the insufflator 20 to detect biocontamination from the patient (e.g., due to backflow). A "biosensor" in this context is any sensor that can directly detect the presence of biocontamination, such as a body fluid or other body substance or a biological agent (e.g., a microbe). Sensors of this type are available from companies such as Agilent Technologies, Inc. of Palo Alto, Calif.

Biosensor 44 is positioned to detect biocontamination entering or about to enter the insulator 20 from the gas supply side at the gas input port 21. As such, biosensor 44 can be located at or just inside the gas input port 21 of the insufflator, as shown, or it can be located outside the insufflator 20 at a convenient location in the external gas supply conduit 4 connected between the gas input port 21 and the gas supply. Biosensor 45 is positioned to detect biocontamination entering or about to enter the insufflator 20 from the gas output side at the gas output port 22. As such, biosensor 45 can be located at or just inside the gas output port 22 of the insufflator, as shown, or it can be located outside the insulator 20 at a convenient location in the external gas conduit 6 connected between the gas output port 22 and the patient (e.g., in the trocar 9).

When biocontamination is detected by biosensor 44, biosensor 44 asserts a signal 46 to the control unit 37, which causes the insufflator 20 to take an appropriate action, which may include any one or more of: outputting an alarm to the user, shutting down the insulator and/or activating some other protection procedure. An alarm in this context may be, for example, an audible and/or visual indication in the GUI and/or a tactile indication to the user. Similarly, when biocontamination is detected by biosensor 45, biosensor 45 asserts a signal 36 to the control unit 37, which causes the insulator 20 to take an appropriate action such as mentioned above.

In embodiments in which biosensor 44 and/or biosensor 45 is external to the insufflator 20, the biosensor signal input may be received by the insulator 20 via one or more physical signal lines (e.g., through the gas input port 21 and/or gas output port 22 and/or a separate signal interface) or via wireless communication links.

The humidifier 26 humidifies the gas to help reduce dehydration of the patient that would be caused by introducing an otherwise dry gas into the body cavity. A user can control the humidifier 26 to control the humidity level, through the GUI.

The insulator 20 further includes a control unit 37 to control the overall operation of the insufflator 20, including operation of flow controller 24, pressure controller 25, heating element 30 and humidifier 26. The control unit 37 may be or may include, for example, one or more programmable microprocessors or microcontrollers, application-specific integrated circuits (ASICs), programmable logic devices (PLDs), or a combination of such devices or similar types of devices commonly used to control electronic and electromechanical devices. The input pressure sensor 31, output pressure sensor 32, output flow sensor 33, humidity sensor 34 and temperature sensor 35 provide their respective output signals to the control unit 37, which are used as feedback to control the gas pressure, flow rate, humidity and temperature, respectively.

The insulator 20 further includes a display unit 38 and various manual input controls 39, for use as mentioned above, as well as a sound unit 40, a network unit 41, memory 42, and an auxiliary unit 43. The sound unit 40 provides audible outputs to the user (e.g., feedback sounds to acknowledge user inputs and/or machine-generated spoken prompts). In certain embodiments, the insufflator 20 may include speech recognition capabilities so as to be capable of responding to spoken commands from a user. In that case, the insulator 20 further includes a sound input device such as a microphone (not shown).

The memory 42 is used to store software and/or data. For example, memory 42 may store software and/or firmware for execution by the control unit 37 to control essentially any function of the insulator 20. In addition, memory 42 may store various user profiles and settings, parameter profiles, etc. Memory 42 may be, for example, essentially any form of random access memory (RAM), read-only memory (ROM) (which may be programmable), flash memory, or other type of memory, or a combination thereof.

The network unit 41, under the control of the appropriately-configured control unit 37, enables the insufflator 20 to communicate with a remote device or person over a network. The network (not shown) may be, for example, a local area network (LAN), a wide area network (WAN), a metropolitan area network (MAN), a global area network (GAN) such as the Internet, or any combination thereof. The network unit 41 may be, for example, a conventional dial-up modem, a cable or Digital Subscriber Line (DSL) modem, an Ethernet adapter, etc.

Thus, an improved insufflator for endoscopy has been described.

Software to implement the techniques introduced here may be stored on a machine-readable medium, such as memory. A "machine-accessible medium", as the term is used herein, includes any mechanism that provides (i.e., stores and/or transmits) information in a form accessible by a machine (e.g., a computer, network device, personal digital assistant (PDA), manufacturing tool, any device with a set of one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The term "logic", as used herein, can include, for example, hardwired circuitry, programmable circuitry, software, or any combination thereof.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. An insufflator to provide a regulated pressurized gas for introduction into the body of a patient during an endoscopic medical procedure, the apparatus comprising:
   a gas input port at which to receive gas from a gas supply;
   a gas output port at which to output the regulated pressurized gas;

an internal flow path coupled between the gas input port and the gas output port and through which to convey the pressurized gas;

a regulator in the internal flow path to regulate the pressurized gas;

a heating element, a venting valve, a pressure relief valve, and an input pressure sensor, each coupled to the internal flow path between the gas input port and the regulator, the heating element to maintain the gas at a predetermined temperature;

a humidifier in the internal flow path to regulate the humidity of the pressurized gas and reduce dehydration in the body of the patient;

a humidity sensor and a temperature sensor, each coupled to the internal flow path between the humidifier and the gas output port;

an output pressure sensor and an output flow sensor each coupled to the gas flow path coupled to the gas flow path between the regulator and the gas output port;

an external gas output conduit coupled to the gas output port to transport the gas to the body of a patient during the endoscopic medical procedure;

a trocar at an end of end of the external gas conduit;

a first biosensor located in the trocar at the end of the external gas conduit to detect the presence of biocontamination during the endoscopic medical procedure and to output a first wireless signal in response thereto;

a second biosensor to detect the presence of biocontamination during the endoscopic medical procedure and to output a second wireless signal in response thereto, wherein the first biosensor is positioned to detect biocontamination entering the insufflator at the gas input port and the second biosensor is positioned within the external gas output conduit to detect biocontamination about to enter the insufflator at the gas output port;

a control unit coupled to the regulator, the humidifier, the humidity sensor, the heating element, the first biosensor, and the second biosensor, the control unit to receive, via a wireless communication link, the first signal and the second signal and, in response to either of the first signal or the second signal, to output an alarm to a user and to cause the insufflator to activate a protection procedure, and wherein the input pressure sensor, output pressure sensor, output flow sensor, humidity sensor, and temperature sensor provide respective output signals to the control unit to control pressure, flow rate, humidity, and temperature of the gas; and a touchscreen display unit coupled to the control unit, the touchscreen display unit to present indicators and a graphical user interface and receive input to control the regulator and the humidifier.

\* \* \* \* \*